United States Patent [19]
Crivello

[11] 4,069,055
[45] * Jan. 17, 1978

[54] PHOTOCURABLE EPOXY COMPOSITIONS CONTAINING GROUP VA ONIUM SALTS

[75] Inventor: James V. Crivello, Elnora, N.Y.

[73] Assignee: General Electric Company, Schenectady, N.Y.

[*] Notice: The portion of the term of this patent subsequent to Nov. 15, 1994, has been disclaimed.

[21] Appl. No.: 638,994

[22] Filed: Dec. 9, 1975

Related U.S. Application Data

[63] Continuation of Ser. No. 466,378, May 2, 1974, abandoned.

[51] Int. Cl.$^2$ .................. G03C 1/68; C09D 11/00; C08F 2/46; C08F 8/18
[52] U.S. Cl. .................. 96/115 R; 96/35.1; 96/85; 106/20; 204/159.14; 204/159.18; 204/159.23; 204/159.24; 260/2 EP; 260/2 EC; 260/47 EC; 260/47 EN
[58] Field of Search .......... 96/115 P, 115 R; 204/159.18, 159.23, 159.24, 159.14; 260/2 EP, 2 EC, 47 EC, 47 EN; 106/20

[56] References Cited
U.S. PATENT DOCUMENTS

| | | | |
|---|---|---|---|
| 3,373,221 | 3/1968 | May | 260/2 EP |
| 3,567,453 | 5/1971 | Borden | 96/115 R |
| 3,637,572 | 1/1972 | Ogata et al. | 260/47 EC |
| 3,660,354 | 5/1972 | Uelzman | 260/47 EC |
| 3,711,390 | 1/1973 | Feinberg | 96/115 P |
| 3,729,313 | 4/1973 | Smith | 96/27 R |
| 3,801,538 | 4/1974 | Morishita et al. | 204/159.18 |
| 3,816,280 | 6/1974 | Watt | 96/115 P |
| 3,826,280 | 7/1974 | Schlesinger | 204/159.23 |
| 3,879,312 | 4/1975 | Udding et al. | 260/2 D |
| 3,979,355 | 9/1976 | Smith | 262/47 EC |

OTHER PUBLICATIONS

Irving et al., Journal Chemical Society, 1960 pp. 2078-2081.
Banks, Organic Review, vol. 66, No. 3, (1966), pp. 243-266.
Schonberg, Preparative Organic Photochemistry, (1968), pp. 455-458.
Knapczyk et al., Journal of Organic Chemistry, vol. 35, No. 8, pp. 2539-2543 (1970).

*Primary Examiner*—Jack P. Brammer
*Attorney, Agent, or Firm*—William A. Teoli; Joseph T. Cohen; Jerome C. Squillaro

[57] ABSTRACT

Cationic polymerization of epoxy resin such as epoxy monomers or prepolymers, can be achieved by use of certain radiation sensitive aromatic onium salts of Group Va elements. Curable compositions are provided which can be used as sealants, coating compounds, encapsulants, etc.

18 Claims, No Drawings

PHOTOCURABLE EPOXY COMPOSITIONS CONTAINING GROUP VA ONIUM SALTS

This is a continuation of application Ser. No. 466,378, filed May 2, 1974 now abandoned.

The present invention relates to epoxy resin compositions which can be cured by exposure to radiant energy.

Epoxy resins have generally been employed in a variety of applications requiring high performance materials. Cure of an epoxy resin can generally be achieved by two package systems based on the incorporation into the resin of active amine containing compounds or carboxylic acid anhydrides. These systems require thorough mixing of the ingredients; in addition, cure time can be several hours.

Another catalyst which can be used to cure epoxy resins as "one package" systems is based on the employment of a Lewis Acid catalyst in the form of an amine complex such as boron trifluoride-monoethyl amine. The Lewis Acid is released on heating; cure takes place within 1 to 8 hours and can require a temperature of 160° C and higher. As a result, these one package epoxy compositions cannot be employed to coat heat sensitive devices such as delicate electronic components. Nor can epoxy monomers having low boiling points be used due to the resulting losses to evaporation during cure.

As shown by Schlesinger, U.S. Pat. No. 3,703,296, certain photosensitive aromatic diazonium salts can be employed to cure epoxy resins. When photolyzed, these aromatic diazonium salts are capable of releasing, in situ, a Lewis Acid catalyst whfich can initiate the rapid polymerization of the epoxy resin. However, even though these one package epoxy resin mixtures can provide fast curing compositions, a stabilizer must be used to minimize cure in the dark during storage of these mixtures. Despite these measures, gellation of the mixture can occur even in the absence of light. In addition, nitrogen is released during UV-cure, which can result in film imperfections. Diazonium salts are generally thermally unstable, rendering the use of such materials hazardous because of the possibility of run-away decomposition.

The present invention is based on the discovery that radiation sensitive aromatic onium salts of Group Va elements, such as

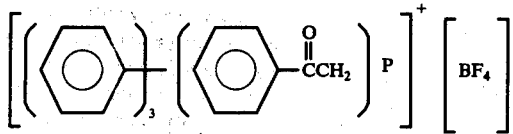

can be incorporated in epoxy resins to provide one package radiation curable compositions which do not require a stabilizer to minimize cure at ambient temperatures during the shelf period, and are free of all of the afore-mentioned disadvantages of the aromatic diazonium salt compositions.

Included by the aromatic Group Va onium salts which can be employed in the curable compositions of the present invention are onium compounds of the formula,

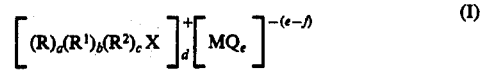

where R is a monovalent aromatic organic radical selected from carbocyclic radicals and heterocyclic radicals, $R^1$ is a monovalent organic aliphatic radical selected from alkyl, alkoxy, cycloalkyl and substituted derivatives thereof, $R^2$ is a polyvalent organic radical forming an aromatic heterocyclic or fused ring structure with X, X is a Group Va element selected from N, P, As, Sb and Bi, M is a metal or metalloid, Q is a halogen radical, $a$ is a whole number equal to 0 to 4 inclusive, $b$ is a whole number equal to 0 to 2 inclusive, $c$ is a whole number equal to 0 to 2 inclusive, and the sum of $a + b + c$ is a value equal to 4 or the valence of X, $d = e - f$ $f$ = valence of M and is an integer equal to from 2 to 7 inclusive $e$ is $>f$ and is an integer having a value up to 8.

Radicals included by R are, for example, $C_{(6-13)}$ aromatic hydrocarbon radicals such as phenyl, tolyl, napthyl, anthryl and such radicals substituted with up to 1 to 4 monovalent radicals such as $C_{(1-8)}$ alkoxy, $C_{(1-8)}$ alkyl, nitro, chloro, hydroxy, etc.; arylacyl radicals such as phenylacyl, etc.; arylalkyl radicals such as phenyl ethyl; aromatic heterocyclic radicals such as pyridyl, furfuryl, etc. $R^1$ radicals include $C_{(1-8)}$ alkyl, $C_{(3-8)}$ cycloalkyl, substituted alkyl such as haloalkyl, for example, chloroethyl; alkoxy such as $OCH_2C_6H_5$ and $OCH_3$; alkoxyalkyl such as $—C_2H_4OCH_3$, etc.; alkylacyl such as $—CH_2COOC_2H_5$; ketoalkyl such as $—CH_2COCH_3$, etc. Radicals included by $R^2$ are, for example,

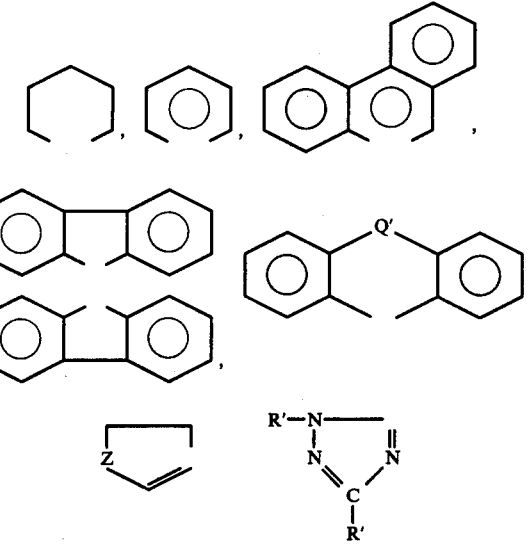

where Q' is selected from O, $CH_2$, N, R and S; Z is selected from —O—, —S— and

and R' is a monovalent radical selected from hydrogen and hydrocarbon. Complex anions included by $MQ_e^{-(e-f)}$ are, for example, $BF_4^-$, $PF_6^-$, $AsF_6^-$, $SbF_6^-$, $FeCl_4^=$, $SnCl_6^-$, $SbCl_6^-$, $BiCl_5^=$, etc., where M is more particularly a transition metal such as Sb, Fe, Sn, Bi, Al, Ga, In, Ti, Zr, Sc, V, Cr, Mn, Co, etc., rare earth elements such as the lanthanides, for example, Ce, Pr, Nd, etc., actinides such as Th, Pa, U, Np, etc. and metalloids such as B, P, As, etc.

There is provided by the present invention curable epoxy compositions comprising, A. an epoxy resin polymerizable to a higher molecular weight state selected from epoxy monomer, epoxy prepolymer, oxirane containing organic polymer and mixtures thereof, and B. an effective amount of a radiation sensitive aromatic onium salt of a Group Va element capable of effecting the cure of (A) by release of a Lewis Acid catalyst when exposed to radiant energy.

Group Va onium salts included by Formula I are, for example,

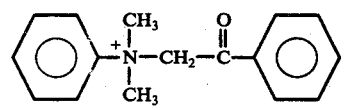 BF$_4^-$,

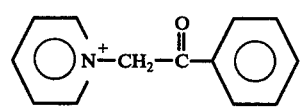 SbF$_6^-$,

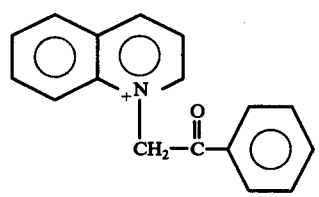 BF$_4^-$,

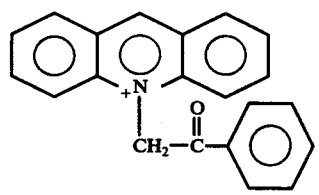 BF$_4^-$,

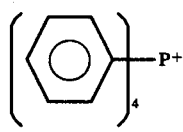 BF$_4^-$,

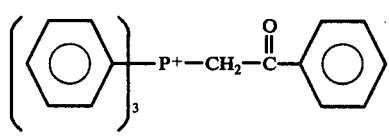 AsF$_6^-$,

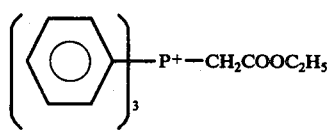 PF$_6^-$,

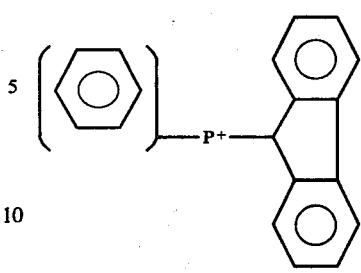 BF$_4^-$,

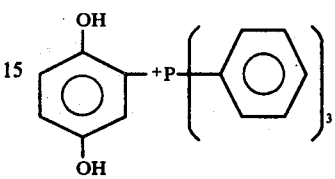 BF$_4^-$,

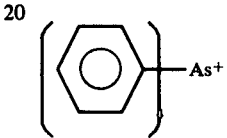 BF$_4^-$,

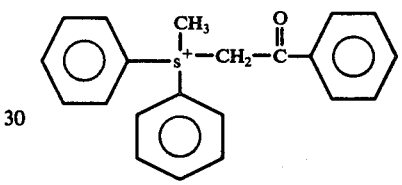 BF$_4^-$,

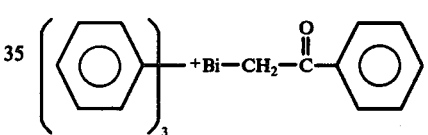 BF$_4^-$.

The Group Va onium salts of formula I are well known. Some of these compounds can be made by the procedures described by J. Goerdeler, Methoden der Organishen Chimie, 11/12, 591–640 (1958) and K. Sasse, ibid., 12/1, 79–112 (1963).

The term "epoxy resin" as utilized in the description of the curable compositions of the present invention, includes any monomeric, dimeric or oligomeric or polymeric epoxy material containing one or a plurality of epoxy functional groups. For example, those resins which result from the reaction of bisphenol-A (4,4′-isopropylidenediphenol) and epichlorohydrin, or by the reaction of low molecular weight phenol-formaldehyde resins (Novolak resins) with epichlorohydrin, can be used alone or in combination with an epoxy containing compound as a reactive diluent. Such diluents as phenyl glycidyl ether, 4-vinylcyclohexene dioxide, limonene dioxide, 1,2-cyclohexane oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers. Other classes of epoxy containing polymers amenable to cure using the above catalysts are epoxy-siloxane resins, epoxy-polyurethanes and epoxypolyesters. Such polymers usually have epoxy functional groups at the ends of their chains. Epoxy-siloxane resins and method for making are more particularly shown by E. P. Plueddemann and G. Fanger, J. Am. Chem. Soc. 81 632-5 (1959). As described in the literature, epoxy resins can also be modified in a number of standard ways such as reactions with amines, carboxylic acids, thiols, phenols, alcohols, etc. as shown in U.S. Pat. Nos. 2,935,488; 3,235,620; 3,369,055; 3,379,653; 3,398,211; 3,403,199; 3,563,850; 3,567,797; 3,677,995, etc. Further examples of epoxy resins which can be used are shown in the Encyclopedia of Polymer Science and Technology, Vol. 6, 1967, Interscience Publishers, New York, pp 209-271.

The curable compositions of the present invention can be made by blending the epoxy resin, which hereinafter will signify epoxy monomer, epoxy prepolymer, epoxy polymer or mixture thereof, with an effective amount of the Group Va onium salt or "onium salt". The resulting curable composition which can be in the form of a varnish having a viscosity of from 1 centipoise to 100,000 centipoises at 25° C or a free flowing powder can be applied to a variety of substrates by conventional means and cured to the tack-free state within 1 second or less to 10 minutes or more.

Depending upon the compatability of the onium salt with the epoxy resin, the group Va onium salt can be dissolved or dispersed therein along with an organic solvent such as nitromethane, acetonitrile, etc., prior to its incorporation. In instances where the epoxy resin is a solid, incorporation of the onium salt can be achieved by dry milling or by melt mixing the resin to effect incorporation of the onium salt.

It has been found that the onium salt also can be generated in situ in the presence of the epoxy resin if desired. For example, an onium salt of the formula,

 (II)

where R, $R^1$, $R^2$, X, $a$, $b$, and $c$ are as previously defined, and $Q''^-$, is an anion such as $Cl^-$, $Br^-$, $I^-$, $F^-$, $HSO_4^-$, $NO_3^-$, etc., can be separately or simultaneously introduced into the epoxy resin with a Lewis Acid salt of the formula

 (III)

where M' is a metal cation, such as $Na^+$, $K^+$, $Ca^{++}$, $Mg^{++}$, $Fe^{++}$, $Ni^{++}$, $Zn^{++}$, $Co^{++}$, etc. and organic cations such as ammonium, pyridinium, etc., and [MQ] is defined in formula I.

Experience has shown that the proportion of onium salt to epoxy resin can vary widely inasmuch as the salt is substantially inert, unless activated. Effective results can be achieved if a proportion of from 0.1% to 15% by weight of onium salt is employed, based on the weight of curable composition. Higher or lower amounts can be used however, depending upon factors such as the nature of epoxy resin, intensity of radiation, cure time desired, etc.

The curable compositions may contain inactive ingredients such as inorganic fillers, dyes, pigments, extenders, viscosity control agents, process aids, UV-screens, etc. in amounts of up to 100 parts filler per 100 of epoxy resin. The curable compositions can be applied to such substrates as metal, rubber, plastic, molded parts or films, paper, wood, glass cloth, concrete, ceramic, etc.

Some of the applications in which the curable compositions of the present invention can be used are, for example, protective, decorative and insulating coatings, potting compounds, printing inks, sealants, adhesives, photoresists, wire insulation, textile coatings, laminates, impregnated tapes, printing plates, etc.

Cure of the curable composition can be achieved by activating the onium salt to provide the release of the Lewis Acid catalyst. Activation of the onium salt can be achieved by heating the composition at a temperature in the range of from 150° to 250° C. Preferably cure can be achieved by exposing the curable composition to radiant energy such as electron beam or ultraviolet light. Electron beam cure can be effected at an accelerator voltage of from about 100 to 1000 KV. Cure of the compositions is preferably achieved by the use of UV irradiation having a wavelength of from 1849 A to 4000 A and an intensity of at least 5,000-80,000 microwatts per cm². The lamp systems used to generate such radiation can consist of ultraviolet lamps such as from 1 to 50 discharge lamps, for example, xenon, metallic halide, metallic arc, such as a low, medium or high pressure mercury vapor discharge lamp, etc. having an operating pressure of from a few millimeters to about 10 atmospheres, etc., can be employed. The lamps can include envelopes capable of transmitting light of a wavelength of from about 1849 A to 4000 A, and preferably 2400 A to 4000 A. The lamp envelope can consist of quartz, such as Spectrocil, or of Pyrex, etc. Typical lamps which can be employed for providing ultraviolet radiation are, for example, medium pressure mercury arcs, such as the GE H3T7 arc and the Hanovia 450 W arc lamp. The cures may be carried out with a combination of various lamps, some or all of which can operate in an inert atmosphere. When using UV lamps, the irradiation flux on the substrate can be at least 0.01 watts per square inch to effect cure of the organic resin within 1 to 20 seconds and permit the cure to be carried on continuously as, for example, in the curing of epoxy-coated steel strip to be taken up at a rate of from 100 to 600 feet per minute. The strip can be cut to a predetermined width for use as transformer laminates, etc. A combination of heat and light may be used to cure reactive compositions. Such a combination of heat and light may serve to reduce the overall cure time.

In order that those skilled in the art will be better able to practice the invention, the following examples are given by way of illustration and not by way of limitation. All parts are by weight.

EXAMPLE 1

A mixture of equal moles of triphenylphosphine and phenacyl bromide in aqueous acetone was stirred for 2 hours until crude triphenylphenacylphosphonium bromide separated. The crude product was isolated by filtration and dried.

An aqueous mixture of approximately equal moles of the above crude aromatic phosphonium bromide and sodium tetrafluoroborate was stirred. Triphenylphenacylfuoroborate separated rapidly since the fluoroborate salts were considerably less soluble than the corresponding bromides. A quantitative yield of triphenylphenyacylfluoroborate having a m.p. of 245°-248° C was obtained.

A curable composition was prepared by incorporating 3% by weight of the above triphenylphenyacylfluoroborate into a 60:40 mixture of the diglycidylether of bisphenol-A and 4-vinylcyclohexene dioxide. A portion of the mixture was allowed to stand in a transparent container for an extended shelf period under normal daylight conditions. There was no change in the viscosity of the mixture.

A portion of the curable composition was applied onto a steel strip as a 0.1 mil film. The treated steel surface was exposed 30 seconds to the ultraviolet radiation of an H3T7 lamp at a distance of 6 inches. A clear, tack-free film was formed which showed no signs of bubbles or other imperfections.

The above treated strip was then immersed in 10C hydrocarbon oil for 48 hours at 120° C to determine its hydrolytic stability in accordance with IFT test ASTM D971-50 Interfacial Tension of Oil Against Water shown on page 322 of the 1970 Annual Book of ASTM Standards, part 17 (November). The initial reading of the oil was about 39.0 dynes/cm. After the test the oil showed an interfacial tension reading of 37. In order to pass, a reading of at least 30 is required.

EXAMPLE 2

A mixture similar to Example 1 was made using triphenylcarbethoxymethyl phosphonium tetrafluoroborate in place of triphenylphenacyltetrafluoroborate. It was found that the epoxy resin cured in 3 minutes to a tack-free state on a glass substrate.

EXAMPLE 3

Additional curable compositions were prepared using the epoxy resin mixture of Example 1 and a variety of phosphonium salts as shown as follows where cation is the organic portion, anion is the Lewis Acid portion, m.p. is the melting point of the crystalline onium salt and "cure time" is the time required to convert the pourable composition to a tack-free rigid state:

| Cation | Anion | m.p.(° C) | Cure Time (min.) |
| --- | --- | --- | --- |
| I (C₆H₅)₄P⁺ | $BF_4^-$ | 350 | 9 |
| II (C₆H₅)₃P⁺—CH₃ | $BF_4^-$ | 125-127 | 10 |
| III (C₆H₅)₃P⁺—CH₂—C(O)—C₆H₅ | $SbF_6^-$ | 149-152 | 1 |
| IV (C₆H₅)₃P⁺—CH₂—C(O)—C₆H₅ | $AsF_6^-$ | 194-197 | 1 |
| V (C₆H₅)₃P⁺—CH₂—C(O)—C₆H₅ | $PF_6^-$ | 203-206 | 1 |
| VI (C₆H₅)₃P⁺—(fluorenyl) | $BF_4^-$ | 297-302 | 5 |
| VII (C₆H₅)₃P⁺—CH(C₆H₅)—CH₂—C(O)—C₆H₅ | $TiF_6^=$ | 220-226 | 10 |

-continued

| | Cation | Anion | m.p.(° C) | Cure Time (min.) |
|---|---|---|---|---|
| VIII | 2,4-dihydroxyphenyl triphenyl phosphonium (HO-C₆H₃(OH)-P⁺(C₆H₅)₃) | BF₄⁻ | 260 | 1.5 |
| IX | 1,4-dihydroxynaphthyl triphenyl phosphonium | BF₄⁻ | 258–263 | 1 |

EXAMPLE 4

The following reaction was carried out in a nitrogen filled dry box. To 5.0 g (0.021 mole) diphenylmethyl arsine there was added 4.17 g (0.021 mole) phenacyl bromide in 25 ml acetone. The resulting pale yellow solution was stirred at room temperature for 6 hours during which the white crystalline diphenylmethyl phenacyl arsonium bromide precipitated. After filtering the product, washing it with water and acetone, 8.3 g (91.5%) product were obtained.

The bromide was dissolved in 50 ml hot distilled water and 2.1 g NaBF₄ were added. A copious white precipitate of the fluoroborate salt formed and was isolated by filtration and washed with water to remove sodium chloride. Analysis: Calc. for $C_{26}H_{20}AsOBF_4$ = %C, 56.0; %H, 4.4. found: %C, 56.1; %H, 4.5.

Three parts of the arsonium fluoroborate was combined with 97 parts of a 70:30 mixture of Dow novolak-epoxy DEN 431 and 4-vinylcyclohexene dioxide. The sensitized mixture was knife coated onto a glass plate so that a 2 mil film was formed. Exposure of the film for 1.5 minutes produced a hard clear film which could not be scratched using a fingernail.

EXAMPLE 5

N-phenacylpyridinium bromide was prepared by slowly adding phenacyl bromide to a stirred flask containing an equimolar quantity of pyridine. The slightly exothermic reaction was accompanied by the precipitation of the solid N-phenacylpyridinium bromide. The salt was then filtered and washed thoroughly with anhydrous ether.

Active photo-catalysts were prepared by dissolving 0.025 mole of the pyridinium salt in 100 ml water. There was then added to respective portions of the pyridinium salt 0.03 mole of NaBF₄, KAsF₆, NaSbF₆ and KPF₆. In all cases white salts precipitated from solution. The salts were washed with distilled water and then dried overnight in vacuo at 60° C.

In the table shown below are recorded the melting points of each of the salts and a comparative cure study of mixture containing 3% of the salts in 4-vinylcyclohexene dioxide. The mixtures were cured to a tack-free state using a GE H3T7 lamp at a distance of 6 inches:

| Salt | m.p. | Time to Cure Tack-Free (min.) |
|---|---|---|
| C₆H₅–CO–CH₂–N⁺(C₅H₅N) BF₄⁻ | 173–175 | 1.5 |
| C₆H₅–CO–CH₂–N⁺(C₅H₅N) PF₆⁻ | 197–203 | 0.3 |
| C₆H₅–CO–CH₂–N⁺(C₅H₅N) AsF₆⁻ | 202–205 | 0.3 |
| C₆H₅–CO–CH₂–N⁺(C₅H₅N) SbF₆⁻ | 166–174 | 1.0 |

EXAMPLE 6

A curable composition was prepared of 97 parts of a mixture of a 60% epoxy novolak having an epoxy equivalent weight of 206 and 40% 4-vinylcyclohexene dioxide with 3 parts N-phenacyacridinium fluoroborate. The mixture was used to impregnate two 6 inch × 6 inch glass cloth squares, which were cut and stacked together. The resulting laminate was cured using a GE H3T7 lamp. Cure time was one minute exposure on each side. A completely dry rigid laminate was obtained which was integrally bonded together. The laminate could be used for the manufacture of circuit boards.

EXAMPLE 7

To 95 g limonene dioxide there was added 2.7 g phenacylpyridinium bromide and 2.1 g sodium hexafluoroarsenate. This composition was thoroughly mixed by rolling on a ball mill for 8 hours. The insoluble salts were then removed by filtration and the remaining epoxy solution tested for photosensitivity. A cured 2 mil solvent resistant film was obtained in 30 seconds using the procedure of Example 1.

EXAMPLE 8

There was added 18.35 g (0.1 mole) 48% aqueous fluoroboric acid to 24.6 g (0.2 mole) 2,6-lutidine-N-oxide dissolved in 100 ml absolute ethanol. A very pale yellow crystalline precipitate was formed on addition and after standing for 30 min. was filtered and thoroughly washed with diethyl ether. Recrystallization from ethanol gave the pure salt.

To a 500 ml flask were added 26.5 g (0.0793 mole) of the amine oxide acid salt in 64.3 ml (1.19 mole) of nitromethane. The solution was stirred at 30°–40° C while 15.6 g (0.159 mole) 1,2-epoxycyclohexane was added dropwise. After stirring for 1 hour, the reaction mixture was cooled to room temperature and poured into 500 ml diethyl ether. The white crystalline product was filtered and washed thoroughly with ether. After recrystallization from absolute ethanol, an 81% yield of product, m.p. 122°–126° C was obtained. Based on method of preparation and elemental analysis for $C_{13}H_{20}NO_2BF_4$, Calc: % C, 50.5; % H, 6.47; % N, 4.53; Found: % C, 50.7; % H, 6.51; % N, 4.50; the product was a compound having the formula,

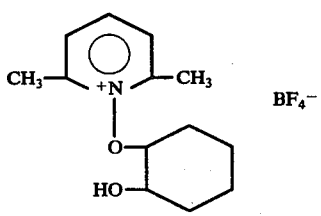

There was added 0.2 part of the above salt to 10 parts of an epoxidized butadiene resin dissolved in 2 g 4-vinylcyclohexene dioxide. After mixing the reagents thoroughly, the mixture was applied to a 1/16 inch thick glass plate as a 1 mil coating. Another plate of glass was placed on top of the first and this assembly exposed to a GE H3T7 medium pressure mercury arc lamp having an intensity of 200 watts/sq. inch at a distance of 3 inches. The total time of exposure was 1 minute. There was obtained a glass laminate.

Based on the characteristics of the resulting laminate, those skilled in the art would know that a similar procedure could be used to make a shatterproof automobile windshield.

EXAMPLE 9

The following table shows several onium salts and their respective melting points. These salts were derived from aromatic nitrogen containing bases by alkylation with phenacyl halides or α-bromotoluene followed by anion exchange with the appropriate inorganic salt in water. There is also shown cure times of 2 mil films of mixtures of 4-vinylcyclohexene dioxide containing 3% by weight of the onium salt, using the procedure of Example I.

| | Cation | Anion | m.p.(° C) | Cure Time(sec.) |
|---|---|---|---|---|
| I | | $BF_4^-$ | 165–169 | 120 |
| II | | $BF_4^-$ | 160–167 | 120 |
| III | | $BF_4^-$ | 209–219 | 20 |
| IV | | $BF_4^-$ | 128–132 | 30 |

| Cation | Anion | m.p.(° C) | Cure Time(sec.) |
|---|---|---|---|
| V (2,6-lutidinium N-oxide with O-CH2-phenyl) | BF4− | 212–217 | 60 |
| VI (2,6-lutidinium N-oxide with O-(2-hydroxycyclohexyl)) | BF4− | 122–126 | 20 |

EXAMPLE 10

Three parts of O-(2-hydroxycyclohexyl)-2,6-lutidinium-N-oxide fluoroborate

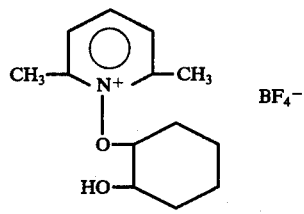

were ground to a fine powder and were intimately mixed with 97 parts Reichhold Epotuf® 37–834 powder coating resin by tumbling them together for 30 minutes. The powder was then electrostatically sprayed onto 3 inch × 6 inch steel panels to form approximately a 2 mil coating using a GEMA model 171 spray gun. Subsequently, the panels were heated briefly to 150° C to fuse the powder and then exposed while hot to a GE H3T7 medium pressure mercury arc lamp at a distance of 3 inches. Cured samples were obtained after a 15 second irradiation.

EXAMPLE 11

There were blended together, 80 parts of bisphenol-A-diglycidylether and a solution composed of 2 parts N-phenacylpyridinium hexafluoroarsenate in 18 parts 4-vinylcyclohexene dioxide. Using a draw-bar, a 1 mil coating was applied to a 3 inch × 6 inch steel panel. A mask was placed over the panel and clamped into place. When this assembly was exposed to ultraviolet light as in example 9 for 20 seconds and then immersed into a bath containing isopropanol, the unexposed portions of the coating were removed leaving a sharp negative image of the mask.

EXAMPLE 12

There was added 10 parts of a solid multifunctional aromatic glycidyl ether having an epoxy equivalent weight of 210–240 to 40 parts limonene dioxide. The mixture was combined with 1 part of N-phenacylpyridinium hexafluorophosphate and stirred at 50° C for 0.5 hour to produce a homogeneous solution of the components. When the mixture was coated on glass using a 0.5 mil draw-bar, and irradiated for 10 seconds at a distance of 3 inches from a GE H3T7 mercury arc lamp operating at an intensity of 200 watts per square inch, a hard cured coating was produced.

EXAMPLE 13

There was added sufficient N-phenacylpyridinium hexafluoroarsenate to a mixture of 67% by weight of a novolak epoxy resin having an epoxy equivalent weight of 172–178, 33% 4-vinylcyclohexene dioxide and 0.5% of a surface active agent to produce a curable mixture having a 1% concentration of ammonium salt. A coating was applied as a 0.1 mil film to 3 inch × 6 inch steel panels and cured for 20 seconds at a distance of 4 inches from a GE H3T7 medium pressure mercury arc lamp. Panels were subsequently immersed for 5 hours at room temperature in methylene chloride; others were immersed for 4 hours in acetone. In all cases, no visible signs of attack on the coating by these agents were observed. The panels were baked for 1 hour at 160° C, then test were run separately in boiling 5% KOH solution for 30 minutes and in boiling distilled water for 4 hours. At the end of these tests, the coatings were intact and showed no signs of degradation.

Although the above examples are limited to only a few of the very many curable compositions and uses thereof which are included within the scope of the present invention, it should be understood that the present invention is intended to cover a much broader class of curable compositions and uses thereof. Those skilled in the art would also know that the curable compositions also cover the use of onium polymers containing Group Va onium functionality as part of the polymer backbone or in the pendant position. In addition, the onium salts of formula I are not intended to include compounds having the —N$^+$=N radical.

What I claim as new and desire to secure by Letters Patent of the U.S. is:

1. Photocurable compositions consisting essentially of
   A. an epoxy resin polymerizable to a higher molecular weight state, and
   B. an effective amount of a photodecomposable aromatic onium salt of a Group Va element capable of effecting the cure of (A) when exposed to radiant energy where the photodecomposable aromatic onium salt of a Group Va element has the formula, $$[(R)_a(R^1)_b(R^2)_cX]^+{}_d[MQ_e]^{-(e-f)},$$

where R is a monovalent aromatic organic radical selected from carbocyclic radicals and heterocyclic radicals, $R^1$ is a monovalent organic aliphatic radical selected from alkyl, alkoxy, cycloalkyl and substituted derivatives thereof, $R^2$ is a polyvalent organic radical forming an aromatic heterocyclic or fused ring structure with X, X is a Group Va element selected from N, P, As, Sb and Bi, M is a metal or metalloid, Q is a halogen radical, $a$ is a whole number equal to 0 to 4 inclusive, $b$ is a whole number equal to 0 to 2 inclusive, $c$ is a whole number equal to 0 to 2 inclusive, and the sum of $a + b + c$ is a value equal to 4 or the valence of X, $d = e - f$
$f$ = valence of M and is an integer equal to from 2 to 7 inclusive
$e$ is $> f$ and is an integer having a value up to 8.

2. A photocurable composition in accordance with claim 1, where the aromatic onium salt is a phosphonium salt.

3. A photocurable composition in accordance with claim 1, where the aromatic onium salt is an ammonium salt.

4. A photocurable composition in accordance with claim 1, where the aromatic onium salt is an arsonium salt.

5. A photocurable composition in accordance with claim 2, where the phosphonium salt is a phenacylphosphonium salt.

6. A photocurable composition in accordance with claim 3, where the ammonium salt is a phenacyl ammonium salt.

7. A photocurable composition in accordance with claim 1, where the aromatic onium salt is a tetrafluoroborate salt.

8. A photocurable composition in accordance with claim 1, where the aromatic onium salt is triphenylphenacylphosphonium fluoroborate.

9. A photocurable composition in accordance with claim 1, where the complex anion of the aromatic onium salt is a hexafluorophosphate.

10. A photocurable composition in accordance with claim 7, where the aromatic onium salt is

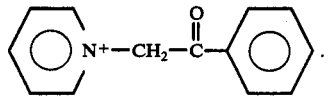

11. A photocurable composition in accordance with claim 1, where the onium salt is prepared in situ.

12. A photocurable composition in accordance with claim 1, where a mixture of onium salts are employed as a Lewis Acid source.

13. A printing ink in accordance with claim 1.

14. A photocurable composition in accordance with claim 1 in the form of a fluid at room temperature.

15. A photocurable composition in accordance with claim 1 in the form of a free-flowing powder.

16. Photocurable compositions in accordance with claim 1, where the aromatic onium salt is triphenylphenacyl phosphonium hexafluoroantimonate.

17. A photocurable composition in accordance with claim 1, where the aromatic onium salt is triphenylphenacyl phosphonium hexafluoroarsenate.

18. A photocurable composition in accordance with claim 9, where the aromatic onium salt is a triphenylphenacyl phosphonium hexafluorophosphate.

* * * * *